United States Patent [19]
Sun et al.

[11] Patent Number: 5,750,713
[45] Date of Patent: May 12, 1998

[54] STEREOSELECTIVE METHOD FOR SYNTHESIZING DOLAPHENINE

[75] Inventors: Xiaoyong Sun, Acton; Yesh P. Sachdeva, Concord; Donna Kaye Wilson, Billerica; Richard L. Gabriel, Swampscott; Siya Ram, Winchester, all of Mass.

[73] Assignee: Pharm-Eco Laboratories, Inc., Lexington, Mass.

[21] Appl. No.: 916,721

[22] Filed: Aug. 18, 1997

Related U.S. Application Data

[63] Continuation of Ser. No. 467,013, Jun. 6, 1995, abandoned.

[51] Int. Cl.$^6$ .................................................. C07D 277/28
[52] U.S. Cl. ........................................... 548/202; 548/204
[58] Field of Search ........................................ 548/202

[56] References Cited

U.S. PATENT DOCUMENTS

| | | | |
|---|---|---|---|
| 4,978,744 | 12/1990 | Pettit et al. | 530/330 |
| 5,200,561 | 4/1993 | Konya | 564/373 |

FOREIGN PATENT DOCUMENTS

| | | |
|---|---|---|
| 0 237 305 | 9/1987 | European Pat. Off. . |
| 0 485 069 | 5/1992 | European Pat. Off. . |
| 05279311 | 10/1993 | Japan . |
| 06340674 | 12/1994 | Japan . |

OTHER PUBLICATIONS

Sakito, Tet. Letters 29(2) 223 (1988).
Dordoni, J. Org. Chem, 56 S294 (1991).
Pettit, G. R., et al., "The Absolute Configuration and Synthesis of Natural (–)–Dolastatin 10," *J. Am. Chem. Soc.*, 111: 5463–5465 (1989).
Irako, N., et al., "A New Efficient Synthesis of (S)–Dolaphenine ((S)–2–Phenyl–1–(2–thiazolyl)ethylamine), the C–Terminal Unit of Dolastatin 10," *Tetrahedron*, 48(35): 7251–7264 (1992).
Shioiri, T., et al., "Stereoselective Synthesis of Dolastatin 10 and Its Congeners," *Tetrahedron*, 49(9) 1913–1924 (1993).
Pettit, G. R., et al., "Structure of the Cyclic Peptide Dolastatin 3 from *Dolabella auricularia*," *J. Am. Chem. Soc.*, 104(3): 905–907 (1982).
Brendenkamp, M. W., et al., "Observations of the Hantzsch Reaction: Synthesis of N–$^t$BOC–S–Dolaphenine," *Synthetic Communications*, 22(21): 3029–3039 (1992).
Fujita, M., et al., "Reduction of Oximes with Hydrosilame/H$^+$ Reagent," *Chemistry Letters*, pp. 837–383 (1986).
Hamada, Y., et al., "New Methods and Reagents in Organic Synthesis. 67. A General Synthesis of Derivatives of Optically Pure 2–(1–Aminoalkyl)thiazole–4–carboxylic Acids," *J. Org. Chem.*, 52: 1252–1255 (1987).
Pettit, G.R., et al., "The Dolastatins 16. Synthesis of Dolaphenine," *Heterocycles*, 39(1): 81–100 (1994).
Brown, H.C. and Krishnamurthy, S., "Boranes for Organic Reductions—A Forty Year Odyssey," *Aldrichimica Acta*, 12(1):167–175 (1979) (Exhibit A).
S. Itsuno, et al., "Asymmetric Synthesis Using Chirally Modified Borohydrides. Part 3. Enantioselective Reduction of Ketones and Oxime Ethers with Reagents Prepared from Borane and Chiral Amino Alcohols," *J. Chem. Soc. Perkin Trans.* 1:2039–2044 (1985).
Y. Komeyoshi, "Chiral Hydroxyphenethylamine Complexes with Borane Derivatives," Chemical Abstracts, 105:114714c 642–643 (1986).

*Primary Examiner*—Robert Gerstl
*Attorney, Agent, or Firm*—Hamilton, Brook, Smith & Reynolds, P.C.

[57] ABSTRACT

The present invention relates to a method for the stereospecific synthesis of an enantiomer of a chiral amine, wherein the chiral amine has the formula $R^1CH(NH_2)R^2$. $R^1$ and $R^2$ are each independently selected from the group consisting of alkyl, aryl and heterocyclic and radicals. This method is particularly useful for stereospecifically synthesizing S-dolaphenine. The method involves contacting a chiral enantiomer of norephedrine with borane, within an aprotic solvent to form a complex for stereospecifically reducing oximes. The complex is then contacted with an oxime, thereby stereospecifically reducing said oxime to form an enantiomer of a chiral amine.

6 Claims, No Drawings

STEREOSELECTIVE METHOD FOR SYNTHESIZING DOLAPHENINE

This application is a continuation of application Ser. No. 08/467,013, filed on Jun. 6, 1995, now abandoned, which is incorporated herein by reference in its entirety.

GOVERNMENT FUNDING

This invention was made with Government support under Contract No. NO1-CM-27764 awarded by the National Institute of Health. The Government has certain rights in the invention.

BACKGROUND OF THE INVENTION

Dolastatin 10 is a highly potent antineoplastic peptide chain of S-dovaline at the C-terminus, S-valine, (3R, 4S, 5S)-dolaisoleuine, (2S,2'R,3'R)-dolaproine and S-dolastatin at the N-terminus. Dolastatin 10 was originally isolated from the Indian Ocean sea hare *Dolabella auricularia*. However, sufficient amounts of Dolastatin 10 cannot reasonably be obtained from *Dolabella a*. Consequently, to support commercial production of Dolastatin 10, various methods have been developed to synthesize the C-terminus unit, S-dolaphenine. However, these methods for synthesizing S-dolaphenine typically require many synthetic steps, often resulting in reduced product yields and/or racemic mixtures of R- and S-dolaphenine.

Therefore, a need exists for a simpler method of stereoselectively forming S-dolaphenine with higher product yields.

SUMMARY OF THE INVENTION

The present invention relates to a method of stereoselectively forming at least one enantiomer of a chiral amine, wherein the chiral amine has the formula $R^1CH(NH_2)(R^2)$. $R^1$ and $R^2$ are each independently selected from the group consisting of lower alkyls, aryl and heterocyclic radicals. This method is particularly useful for stereoselectively synthesizing S-dolaphenine. The method involves contacting at least one diastereomer of norephedrine with borane, wherein the borane is complexed with an aprotic solvent, to form a norephedrine complex for stereoselectively reducing oximes. The norephedrine complex is then contacted with an oxime, having the formula $R^1C(=NOR^3)R^2$ wherein $R^3$ is an alkyl or aryl radical, within an aprotic solvent to stereoselectively reducing said oxime to form at least one enantiomer of a chiral amine.

This invention has the advantage of providing an economical, simpler method of forming relatively pure enantiomers of chiral amines, such as S-dolaphenine in higher yields.

DETAILED DESCRIPTION OF THE INVENTION

The terms stereoselective, stereoisomer, chiral and enantiomer are as classically defined in the art. For instance, stereoisomers are configurational isomers that are different from each other only in the way the atoms are oriented in space, but are like one another with respect to which atoms are joined to which other atoms. Stereoisomers which are not superimposable upon their mirror images are chiral. Further, such non-superimposable, mirror-image stereoisomers are enantiomers.

Enantiomers are distinguishable by optical activity and configuration. An amine having the formula $R^1CH(NH_2)$ ($R^2$), wherein the amine is chiral (thus $R^1$ is not the same as $R^2$) has two enantiomers having different configurations about the chiral center (the carbon of the CH group), the R-configured isomer and the S-configured isomer.

A lower alkyl is defined herein as a $C_1$ to $C_{10}$ branched, cyclic or straight-chained aliphatic hydrocarbon, which may optionally be saturated or unsaturated, and which may optionally be substituted with an aryl and/or heterocyclic group and/or one or more times with a whole group. Examples of suitable alkyl groups include, for instance, methyl, ethyl, propyl, butyl and iso-butyl groups. A preferred substituted alkyl, of this invention, is a benzyl group.

Aryl groups of the present invention include $C_6$ to $C_{14}$ aryl radicals. An aryl group may also be optionally substituted one or more times with a $C_1$ to $C_4$ alkyl, a $C_1$ to $C_4$ alkoxy, a phenyl, a phenyloxy or a halo group. Examples of suitable aryl groups include phenyl and naphthyl groups, and of substituted aryl groups include dibenzyl, chlorophenyl and methylphenyl groups.

Further, heterocyclic radicals are defined as $C_3$ to $C_{12}$ carbon rings containing from 1 to 3 heteroatoms, such as nitrogen, oxygen and/or sulfur, within the carbon ring. A heterocyclic radical may optionally be substituted one or more times with a $C_1$ to $C_4$ alkyl group or a halo group. Suitable heterocyclic radicals include, for instance, imidazolyl, pyridyl, pyrryl, thiophenyl, pyrimidyl, thiazolyl and furyl groups.

The norephedrine used in this method typically comprises (1S,2R)-(+)-norephedrine, (1R,2S)-(−)-norephedrine, or mixtures thereof. It is understood that the norephedrine used can be in a solid state, or preferably dissolved in a suitable aprotic solvent, such as tetrahydrofuran (THF).

The borane used in the method of invention is in the form of borane complexed with a aprotic solvent, such as THF, pyridine, poly(2-vinyl pyridine), 1,4-oxathiane, 2,6-lutidine or 4-methylmorpholine. These complexed-boranes are commercially available from Aldrich Chemicals (Milwaukee, Wis.). The preferred complexed-borane is a borane-THF complex. An even more preferred borane-complex comprises a 1.0M solution of borane-THF complex in THF.

Either (1S,2R)-(+)-norephedrine, or (1R,2S)-(−)-norephedrine, or a combination thereof can be contacted with complexed-borane to form a solution for stereoselectively reducing oximes. In this method, norephedrine is contacted with a complexed-borane under anhydrous conditions to form said stereoselective reducing solution.

Anhydrous conditions, as defined herein, means no water is present with the reagents or solvent and that the reaction is performed in an inert atmosphere, such as under argon or nitrogen. Preferably, no significant amount of free oxygen is present under anhydrous conditions.

Generally, from about 0.1 moles to about 10 moles, or more, of complexed-borane are used per mole of norephedrine. It is preferred to use an amount of complexed-borane in excess of 2 moles of complexed-borane per mole of norephedrine. To control the rate of energy released upon contacting complexed-borane with norephedrine, the rate of addition can be slowed, such as by dropwise addition, and/or the reaction can be performed under cold conditions, such as below 0° C. When using borane-THF complex, it is preferred to perform the reaction at a temperature of about −40° C. or less.

To stereoselectively form at least one enantiomer of the chiral amine product, the stereoselective reducing solution is contacted with an oxime, having the formula $R^1C(=NOR^3)$ $R^2$. Typically, the stereoselective reducing solution is formed under anhydrous conditions.

3

The oxime used can be in a solid or liquid form or can be in solution within an aprotic solvent. Typically, from about 0.1 moles to about 1.0 moles of oxime are used per mole of norephedrine in the stereoselective reducing solution. Preferably, from about 0.3 moles to about 0.5 moles of oxime are used per mole of norephedrine.

In one embodiment of the method of this invention, a first enantiomer of said chiral amine is stereoselectively formed either by contacting the anti-oxime isomer with a first stereoselective reducing solution, formed using (1S,2R)-(+)-norephedrine, or by contacting the syn-oxime with a second stereoselective reducing solution, formed using (1R,2S)-(−)-norephedrine.

In a preferred embodiment, the first chiral amine enantiomer comprises S-dolaphenine. S-dolaphenine is stereoselectively formed according to this method by contacting anti-benzyl 2-thiazolyl ketone O-methyloxime with the first stereoselective reducing solution or alternatively, by contacting syn-benzyl 2-thiazolyl ketone O-methyloxime with the second stereoselective reducing solution. See Example 3 for further description of the synthesis of S-dolaphenine from the syn-oxime.

In another embodiment, a second enantiomer of said chiral amine can be formed by contacting either the syn-oxime with said first stereoselective reducing solution, or the anti-oxime with said second stereoselective reducing solution.

In yet another embodiment, the second chiral amine enantiomer comprises R-dolaphenine. R-dolaphenine is stereoselectively formed according to this method by contacting syn-benzyl 2-thiazolyl ketone O-methyloxime with the first stereoselective reducing solution or alternatively, by contacting anti-benzyl 2-thiazolyl ketone O-methyloxime with the second stereoselective reducing solution. See Example 5 for further description of the synthesis of R-dolaphenine from the anti-oxime.

In a further embodiment, an enantiomeric mixture of the first and the second enantiomers of the chiral amine is formed by contacting a single oxime isomer (anti- or syn-) with a third stereoselective reducing solution, formed using both (1R,2S)-(+)-norephedrine and (1S,2R)-(−)-norephedrine. Alternatively, an enantiomeric mixture is formed by contacting the first or the second stereoselective reducing solution with a mixture of the anti-oxime and the syn-oxime. Example 7 further describes forming an enantiomeric mixture of S-dolaphenine and R-dolaphenine by contacting a mixture of the syn-isomer and the anti-isomer of benzyl 2-thiazolyl ketone O-methyloxime with the first reducing solution.

In yet another embodiment, an enantiomeric mixture is formed by contacting the third stereoselective reducing solution with the anti-oxime, the syn-oxime or a mixture thereof.

Enantiomeric mixtures of different chiral amine enantiomers can then be separated by means known in the art, such as by resolution with tartaric acid. Example 8, further describes the resolution of a racemic solution of dolaphenine, with tartaric acid, into S-dolaphenine and R-dolaphenine.

In one embodiment, a protecting group, for instance tert-butoxycarbonyl ("BOC"), carbobenzyloxy ("CBZ"), or 9-fluorenylmethoxycarbonyl ("FMOC"), is substituted into the amino group of a chiral amine enantiomer by means known in the art. Examples 4 and 6 describe protecting the amino groups of S-dolaphenine and R-dolaphenine, respectively.

4

Examples of methods to form a suitable oxime for use in this method, include contacting a ketone ($R^1C(O)R^2$) with a hydroxylamine derivative ($R^3ONH_2$), or a salt thereof, in an aprotic solvent to form an oxime of the formula $R^1C(=NOR^3)R^2$.

In the method wherein at least one chiral enantiomer of dolaphenine is formed, the oxime used comprises at least one isomer of benzyl 2-thiazole ketone O-methyloxime. In one embodiment benzyl 2-thiazole ketone O-methyloxime is formed from benzyl 2-thiazole ketone. Specifically, benzyl 2-thiazolyl ketone (7.0 g, 31 mmol) in pyridine (40 mL), O-methylhydroxylamine hydrochloride (6.5 g, 32 mmol) was added portionwise to form a reaction mixture. The reaction mixture was stirred at room temperature for 6 hour.

Methods of forming a suitable ketone include, for example, contacting an acid chloride ($R^1C(O)Cl$) with a silyl compound ($Si(R^4)_3R^2$) within an aprotic solvent. Each $R^4$ is independently selected from lower alkyl, aryl and heterocyclic radicals.

In one embodiment, benzyl 2-thiazolyl ketone is formed from 2-trimethylsilylthiazole. To a stirred solution of 2-trimethylsilylthiazole (14.4 g, 63 mmol), dissolved in methylene chloride (40 mL) and cooled in an ice bath, phenylacetyl chloride (19.9 g, 136 mmol), dissolved in methylene chloride (40 mL), was added dropwise to form a reaction mixture. After addition, the reaction mixture was warmed to room temperature and stirred for 20 hours.

The invention will now be further and specifically described by the following examples.

EXAMPLE 1

Synthesis of Benzyl 2-thiazolyl ketone

To a stirred solution of 2-trimethylsilylthiazole (14.4 g, 63 mmol), dissolved in methylene chloride (40 mL) and cooled in an ice bath, phenylacetyl chloride (19.9 g, 136 mmol), dissolved in methylene chloride (40 mL), was added dropwise to form a reaction mixture. After addition, the reaction mixture was warmed to room temperature and stirred for 20 hours. The reaction mixture was then quenched with saturated $NaHCO_3$ aqueous solution. The organic layer was separated and washed with 1N NaOH solution, water, saturated aqueous NaCl, and dried over anhydrous $Na_2SO_4$. After filtration, concentration of the organic layer, in vacuo, gave an orange oil-like residue, which was purified by silica gel column chromatography with $CH_2Cl_2$/hexane (9:1, $R_f$=0.51) to give benzyl 2-thiazoly ketone (9.0 g, 50%) as a pale yellow solid, which was then recrystallized from EtOAc/hexane. mp 60.5°–61.5° C. IR (KBr):1680, 1370, 720 cm$^{-1}$. $^1$H-NMR (CDCl$_3$) δ: 4.50 (s,2H), 7.1 (m,5H), 7.54 (d, 1H,J=3 Hz), 8.10 (d,1H,J=3 Hz).

EXAMPLE 2

Synthesis of Benzyl 2-thiazolyl ketone O-methyloxime

To a solution of benzyl 2-thiazolyl ketone (7.0 g, 31 mmol) in pyridine (40 mL), O-methylhydroxylamine hydrochloride (6.5 g, 32 mmol) was added portionwise to form a reaction mixture. The reaction mixture was stirred at room temperature for 6 hours. The reaction mixture was then concentrated in vacuo and the residue was diluted with water (300 mL) and extracted with EtOAc (100 mL×3). The organic layers were combined and washed with saturated aqueous $NaHCO_3$ (60 mL), water (60 mL), and saturated aqueous NaCl (60 mL). The organic solution was dried over $Na_2SO_4$ and concentrated, in vacuo, to provide a residue, which was purified by silica gel column chromatography. Elution with $CH_2Cl_2$/hexane (3:7) gave the desired anti-oxime (1.0 g) as a light pale yellow oil, with the ratio of anti/syn-oxime isomer produced at 91%. $R_f$anti=0.51, $R_f$syn=0.63 [silica gel/$CH_2Cl_2$:hexane(9:1)]. IR(neat): 1600, 1490, 1060, 1000, 870, 710, 700 $cm^{-1}$. $^1$H-NMR of anti-oxime ($CDCl_3$) δ: 4.12 (s,3H), 4.25 (s,2H), 7.17–7.41 (m,5H), 7.49 (d,1H,J=3 Hz), 7.95 (d,1H,J=3 Hz). $^1$H-NMR of syn-oxime ($CDCl_3$) δ: 4.05 (s,3H), 4.30 (s,2H), 7.17–7.41 (m,6H), 7.65 (d,1H,J=3 Hz).

EXAMPLE 3

Synthesis of S-(+)-dolaphenine [S-(+)-2-Phenyl-1-(2-thiazolyl)ethylamine]

Borane-THF complex (1.0M solution in THF, 44 mL, 44 mmol) was added dropwise at −78° C. to a solution of (1S, 2R)-(+)-norephedrine (3.3 g, 21.5 mmol) in THF (30 mL) while maintaining an argon atmosphere to form a borane-(1S, 2R)-(+)-norephedrine complex in solution. The resulting solution was warmed to room temperature. A solution of anti-oxime (2.0 g, 8.6 mmol) in THF (20 mL) was then added dropwise. The resulting mixture was stirred at room temperature for 16 hours and refluxed for 4 hours. After the reaction mixture was cooled to room temperature, it was gradually acidified with 18% HCl (60 mL) to convert the amine to a salt such that during chromatography the amine can be separated from norephedrine, stirred at room temperature for 2 hours, and concentrated under vacuum. The residue was diluted with water and made basic with solid $NaHCO_3$ at 0° C. until the pH was 9. The mixture was extracted with EtOAc (60 mL×3). The organic layer was then dried over anhydrous $Na_2SO_4$. Evaporation of the solvent, under vacuum, gave an orange oil which was purified by silica gel column chromatography. Elution with EtOAc/hexane (3:7) and then with EtOAc gave S-(+)-dolaphenine as pale yellow oil (1.5 g, 60%). [a]$^{23}$=+13°(c=1, $CH_3OH$). $R_f$=0.27 (silica gel/EtOAc). IR (neat): 1600, 1490, 1442, 720, 690 $cm^{-1}$. $^1$H-NMR ($CDCl_3$, δ: 1.70 (s,2H), 2.90 (dd,1H), 3.41 (dd,1H), 4.55 (dd,1H), 7.25 (m,6H), 7.75 (d,1H).

Elemental analysis had predicted values of C 64.67%, H 5.92% and N 13.71% and found C 64.48%, H 6.06, and N 13.52%.

EXAMPLE 4

Synthesis of N-CBZ-S-(−)-Dolaphenine

To a vigorously stirred solution of S-(+)-dolaphenine (0.12 g, 0.58 mmol) in EtOAc (6 mL) and saturated aqueous $NaHCO_3$ (1 mL), benzyl chloroformate (0.18 g, 1.0 mmol), at room temperature, was added. The reaction mixture was stirred for 3 hours. The organic layer was separated, washed with saturated aqueous $NaHCO_3$, and dried over anhydrous $Na_2SO_4$. After filtration and evaporation, the residue was purified by silica gel column chromatography. Elution with EtOAc/hexane (3:7) gave a white solid of N-CBZ-S-(−)-amine (0.14 g, 80%), mp 74°–75.5° C. [a]$^{23}$=−20° (c=0.7, $CH_3OH$). $R_f$=0.39 [silica gel/EtOAc:hexane (7:3)]. IR (KBr) :3200, 1700, 1550, 1500, 1250, 1010 $cm^{-1}$. $^1$H-NMR ($CDCl_3$) δ: 3.3 (d,2H,J=6.6 Hz), 5.09 (s,2H), 5.37 (dd, 1H,J=7.9 Hz), 5.58 (d,1H,J=7.9 Hz), 7.05 (d,1H,J=3.3 Hz), 7.19–7.26 (m,5H), 7.32 (s,5H), 7.74 (d,1H,J=3.3 Hz).

EXAMPLE 5

Synthesis of R-(−)-dolaphenine [R-(−)-2-phenyl-1-(2-thiazolyl)ethylamine]

To a solution of (1R,2S)-(−)-norephedrine (5.5 g, 36.5 mmol), in THF (80 mL), borane-THF complex (1.0M solution in THF, 109 mL, 109 mmol) at −78° C., was added dropwise under argon atmosphere. The resulting solution was warmed to room temperature. A solution of anti-oxime (3.4 g, 14.6 mmol), in THF (40 mL), was then added dropwise. The resulting mixture was stirred at room temperature for 16 hours and refluxed for 4 hours. After cooling to room temperature, the reaction mixture was gradually acidified with 18% HCl (60 mL), stirred at room temperature for 2 hours and concentrated in vacuo. The residue was diluted with water and basified with solid $NaHCO_3$ at 0° C. until the pH was 9, and extracted with EtOAc (60 mL×3). The organic layer was dried over $Na_2SO_4$. Concentration, in vacuo, gave an orange oil, which was purified by silica gel column with EtOAc/hexane (3:7) first and then EtOAc. R-(−)-dolaphenine was obtained as orange oil (1.5 g, 52%). [α]$^{23}$=−13° (c=1, $CH_3OH$). $R_f$=0.27 (silica gel/EtOAc). IR (neat):1600, 1490, 1442, 720, 690 $cm^{-1}$. $^1$H-NMR ($CDCl_3$) δ: 1.70 (s,2H), 2.90 (dd,1H), 3.41 (dd,1H), 4.55 (dd,1H), 7.25 (m,6H), 7.75 (d,1H).

Elemental analysis had predicted values C 64.67%, H 5.92% and N 13.71% and found C 64.49%, H 6.03, and N 13.48%.

EXAMPLE 6

N-Boc-R-(+)-dolaphenine

To a vigorously stirred solution of R-(−)-dolaphenine (0.056 g, 0.27 mmol), in THF (2 mL), di-tert-butyl-dicarbonate (0.073 g, 0.33 mmol) in THF (2 mL), was added at an ice bath temperature (about 2° to 0° C.). The reaction mixture was stirred for half an hour and warmed to room temperature. The reaction mixture was then stirred at room temperature for 16 hours. The solvent was removed in a vacuum, the residue was diluted with water, and extracted with EtOAc (20 mL×2). The organic layer was dried over anhydrous $Na_2SO_4$. After evaporation of the solvent, the residue was purified by silica gel column (EtOAc-hexane (3:7)). The N-Boc derivative was obtained as a white solid (40 mg, 46%). [α]$^{23}$=+23° (c=1, $CH_3OH$); $R_f$=0.4 (silica/gel/EtOAc-hexane; 3:7). IR (KBr):3220, 1700, 1515, 1250, 1160, 1010 $cm^{-1}$. $^1$H NMR ($CDCl_3$) δ: 7.8 (d,1H), 7.3–7.1 (m,6H), 5.3 (m,1H), 3.3 (d,2H), 1.61 (s,1H), 1.4 (s,9H).

EXAMPLE 7

Synthesis of Racemic Dolaphenine

To a solution of (1S,2R)-(+)-norephedrine (10.3 g, 68.9 mmol), in THF (120 mL), borane-THF complex (1.0M solution in THF (160 mL, 160 mmol) was added dropwise at −78° C. under an argon atmosphere. The resulting solution was then warmed to room temperature. A solution of anti- and syn-oxime [3:1 mixture](6.1 g, 27.5 mmol) in THF (80 mL) was then added dropwise. The resulting mixture was stirred at room temperature for 42 hours and refluxed for 8 hours. After cooling to room temperature, the reaction mixture was gradually acidified with 18% HCl (120 mL), stirred for 2 hours, and concentrated in vacuo. The residue was diluted with water and basified with solid $NaHCO_3$ at 0° C. until pH was 9, and extracted with EtOAc (3×60 mL). The organic layer was dried over $Na_2SO_4$. After filtration, concentration of organic filtrate, under vacuum gave an orange oil, which was purified by silica gel column by eluting with EtOAc/hexane (3:7) first and then EtOAc. Racemic "dolaphenine" was obtained as pale yellow oil (3.3 g, 61%) which contained significant amount of S-(+)-dolaphenine. [α]$^{23}$=+7.3°.

EXAMPLE 8

Resolution of Racemic Dolaphenine with R,R-Tartaric Acid

R,R-tartaric acid (3.5 g, 23 mmol) was added to the solution of racemic dolaphenine (3.3 g, 16.2 mmol) in ethanol (20 mL). The suspension was stirred at room temperature overnight. Then 2 mL water was added to dilute the suspension. After filtration, white solid S-amine-R,R-tartrate was restirred in the 20 mL solvent of EtOH/H$_2$O (8:1) for one hour. After filtration, the white solid (4.2 g, 74%, mp=180° C.) was dried under vacuo. The resulting solid was dissolved in small amount of water and saturated aqueous NaCO$_3$ was added and stirred for half hour, extracted with EtOAc (60 mL×3). The organic layer was washed with water and dried over anhydrous Na$_2$SO$_4$. After filtration and evaporation, pure S-(+)-dolaphenine as pale-yellow oil (2.1 g, 88%) was obtained in a ratio with R-(−)-dolaphenine of about 3–4:1. [a]$^{23}$=+13° (c=1, CH$_3$OH).

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of stereoselectively forming one enantiomer of a compound represented by the following structural formula:

wherein R$^1$ and R$^2$ are each independently selected from the group consisting of a lower alkyl, an aryl and a heterocyclic radical, and wherein R$^1$ and R$^2$ are not the same, comprising the steps of:

a) reacting a ketone represented by the following structural formula:

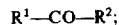

with R$^3$ONH$_2$, or a salt thereof, wherein R$^3$ is an alkyl or aryl radical, to form syn and anti isomers of an oxime represented by the following structural formula:

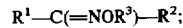

b) separating syn and anti isomers of the oxime formed in step a); and c) reacting the syn isomer of the oxime with a reducing solution formed by mixing (+)-norephedrine with borane complexed with an aprotic solvent, or reacting the anti isomer of the oxime with a reducing solution formed by mixing (−)-norephedrine with borane completed with an aprotic solvent to stereoselectively form an enantiomer of the compound; or d) reacting the anti isomer of the oxime with a reducing solution formed by mixing (+)-norephedrine with borane completed with an aprotic solvent, or reacting the syn isomer of (−)-norephedrine with borane complexed with an aprotic solvent to stereoselectively form the other enantiomer of the compound.

2. A method of stereoselectively forming S-dolaphenine or R-dolaphenine, comprising the steps of:

a) reacting benzyl 2-thiazole ketone with R$^3$ONH$_2$ or a salt thereof, wherein R$^3$ is an alkyl or aryl radical, to form syn and anti isomers of an oxime represented by the following structural formula:

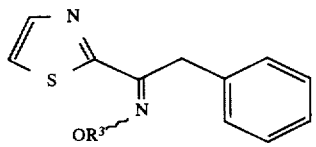

b) separating the syn and anti isomers of the oxime formed in step a); and c) reacting the syn isomer of the oxime with a reducing solution formed by mixing (−)-norephedrine with borane complexed with an aprotic solvent, or reacting the anti isomer of the oxime with a reducing solution formed by mixing (+)-norephedrine with borane complexed to stereoselectively form S-dolaphenine; or d) reacting the anti isomer of the oxime with a reducing solution formed by mixing (−)-norephedrine with borane complexed with an aprotic solvent, or reacting the syn isomer of the oxime with a reducing solution formed by mixing (+)-norephedrine with borane complexed to stereoselectively form R-dolaphenine.

3. The method of claim 2 wherein R$^3$ is methyl.

4. The method of claim 2 wherein the aprotic solvent in steps c) and d) is tetrahydrofuran, pyridine, 1,4-oxathiane, 2,6-lutidine or 4-methylmorpholine.

5. The method of claim 2 wherein benzyl 2-thiazole ketone is prepared by reacting reacting phenylacetyl chloride with 2-(R$^4_3$Si-)thiazole to form benzyl 2-thiazole ketone, wherein each R$^4$ is independently selected from the group consisting of a lower alkyl, an aryl and a heterocyclic radical.

6. The method of claim 5 wherein each R$^4$ is methyl.

* * * * *

UNITED STATES PATENT AND TRADEMARK OFFICE
CERTIFICATE OF CORRECTION

PATENT NO. : 5,750,713
DATED : May 12, 1998
INVENTOR(S) : Xiaoyong Sun, Yesh P. Sachdeva, Donna Kaye Wilson, Richard L. Gabriel and Siya Ram It is certified that error appears in the above-identified patent and that said Letters Patent is hereby corrected as shown below:

In Claim 1, at Column 8, lines 2-3, delete "completed" and insert --complexed--;

In Claim 1, at Column 8, line 7, delete "completed" and insert --complexed--; and In Claim 5, line 2, delete "reacting reacting" and insert --reacting--.

Signed and Sealed this

Eleventh Day of August 1998

Attest:

*Attesting Officer*

BRUCE LEHMAN
*Commissioner of Patents and Trademarks*